US00PP07900P

United States Patent [19]

Williams

[11] Patent Number: Plant 7,900

[45] Date of Patent: Jul. 7, 1992

[54] MINIATURE ROSE PLANT NAMED 'MICCAR'

[76] Inventor: Michael C. Williams, P.O. Box 203, Austin St., Cross Hill, S.C. 29332

[21] Appl. No.: 636,922

[22] Filed: Jan. 2, 1991

[51] Int. Cl.[5] ..... A01H 5/00

[52] U.S. Cl. ..... Plt./10

[58] Field of Search ..... Plt. 7, 8, 9, 10

*Primary Examiner*—James R. Feyrer

[57] ABSTRACT

A new and distinct variety of miniature rose plant characterized by (1) bright red buds and blooms with a yellow base and (2) a compact plant with abundant glossy green foliage.

1 Drawing Sheet

1

Rose plant: Miccar.
Commercial synonym: Carolina Morning.

The present invention relates to a new and distinct variety of rose plant of the miniature rose class, which was originated by my crossing as seed parent the miniature rose known as Rise 'n' Shine (U.S. Plant Pat. No. 4,231) and a miniature rose Rainbow's End (U.S. Plant Pat. No. 5,482) as pollen parent.

Among the novel characteristics possessed by this new variety which distinguishes it from its parents and all other varieties of which I am aware are (1) high-centered blooms of medium red with a yellow base, (2) an abundance of bloom with flowers usually borne singly, (3) a very slight fruity fragrance, (4) a well proportioned plant which is vigorous and shows off its blooms well against its dark green glossy foliage, and (5) a plant which grows well both in the greenhouse and outdoors, is good for growing in pots, and provides excellent garden decoration as well as cut flowers.

The present variety of miniature rose was originated by me in Laurens County, S.C. Carefully controlled conditions and asexual reproduction by cuttings of the new variety as performed by me in Laurens County, S.C., show that the foregoing and other distinguishing characteristics come true to form and are established and transmitted through succeeding propagations.

The accompanying photograph shows typical specimens of the vegetative growth and flowers of the new variety in different stages of development and as depicted in color as nearly true as it is reasonably possible to make the same in a color photograph of this character.

The following is a detailed description of my new rose variety, with color terminology in accordance with Royal Horticultural Society Colour Chart except where common dictionary terms of color definition are employed.

Type: Hardy, dwarf, upright, seedling, greenhouse, outdoors, cut flowers, garden decoration, potted plant.
Class: miniature.
International identifications:
*Variety.*—Miccar.
*Commercial synonym.13* Carolina Morning.

2

THE FLOWER

Observations were made from specimen grown outdoors in Laurens County, S.C., USA during the summer of 1990.

Type: Miniature
Blooming habit: Recurrent.
Bud:
*Size.*—Medium for miniature.
*Form.*—Pear-shaped.
*Color.*—When sepals first divide: red (45-A). When petals begin to unfurl: Inside: Red (45-A) to yellow (2-A) at the base. Outside: Red (45-A) to yellow (2-A) at the base. When half-blown: Inside: All petals red (45-A) from tip to ¾ way down where color changes to yellow (2-A). Reverse side of petals: Same as inside.
*Sepals.*—As long as the bud, thin and pointed.
*Peduncle.*—Average length 1", smooth, erect and stable, light green color.
Bloom:
*Size.*—1" to 1½" when fully expanded.
*Borne.*—Singly. Occasionally there may be two sidebuds.
*Form.*—High centered.
*Petalage.*—About 22.
*Color.*—During first two days: Inner petals at center of flower: Red (45-B). Outer petals: Red (45-B). Base of petals (point of attachment): Yellow (2-A). Reverse of petals: Red (45-B) to yellow (1-A) at base. General tonality from a distance: Red (45-B).
*Color change.*—Red (45-B) to red (45-C). General tonality: Red 45-C. After three or more days: Red (45-D).
Petals:
*Texture.*—Thick.
*Appearance.*—Inside: Slightly velvety. Outside: Slightly satiny.
*Form.*—Oval.
*Arrangement.*—Regularly arranged.
*Petaloids in center.*—Very few.
*Persistence.*—Drop cleanly except in cool damp conditions.
*Fragrance.*—Slight fruity fragrance.
*Lasting quality.*—Slow opening on plant, keeps long in refrigerator, good as cut flower and as pot plant.

REPRODUCTIVE ORGANS

Stamens, filaments and anthers:
*Arrangement.*—Bunched tightly around styles.
*Color.*—Yellow.
Pollen: Yellow.
Styles: Even 3/16" length, thin, tightly bunched.
Stigmas:
*Color.*—Pale green.
Hips: None.

PLANT

Form: Upright.
Growth: Vigorous and uniform branching.
*Height attained.*—15" to 18".
Foliage: Mostly 5 leaflets.
Size: Medium for miniature.
Quantity: Abundant.
Color:
*New foliage.*—Upper side: Dark green with red edges and veins. Under side: Lighter shade of green with red edges and veins.
*Old foliage.*—Upper side: Dark semi-glossy green. Under side: Flat green and lighter than upper side.
Shape: Oval, pointed.
Texture:
*Upper side.*—Smooth, healthy appearance.
*Under side.*—Raised veins.
Edge: Serrated.
Leaf stem:

*Color.*—Green. Under side: Paler green.
Stipules: Medium, ⅛" pointed.
Disease resistance:
*Blackspot.*—Good.
*Mildew.*—Average.
*Rust.*—Good.
Wood:
*New wood.*—Color: Brownish. Bark: Smooth.
*Old wood.*—Color: Medium green. Bark: Smooth.
Thorns:
*Quantity.*—Several on main cane, with few on laterals.
*Form.*—Needle shaped with flat base.
*Length.*—Short, ¼".
*Color when young.*—Brown.
*Position.*—Regular.
Prickles:
*Quantity.*—None on main canes or on laterals.
Winter hardiness: Needs some protection at 10 degrees or lower Fahrenheit. Can use mound of soil or leaves.

I claim:

1. A new and distinct variety of rose plant of the miniature rose class, substantially as herein shown and described, characterized particularly by high-centered blooms of medium red coloring, with firm, thick petals, borne freely on a compact plant with glossy dark green new foliage and semi-glossy darker green old foliage, said plant being easy to propagate from cuttings, and said blooms being long-lasting on the plant and as cut flowers.

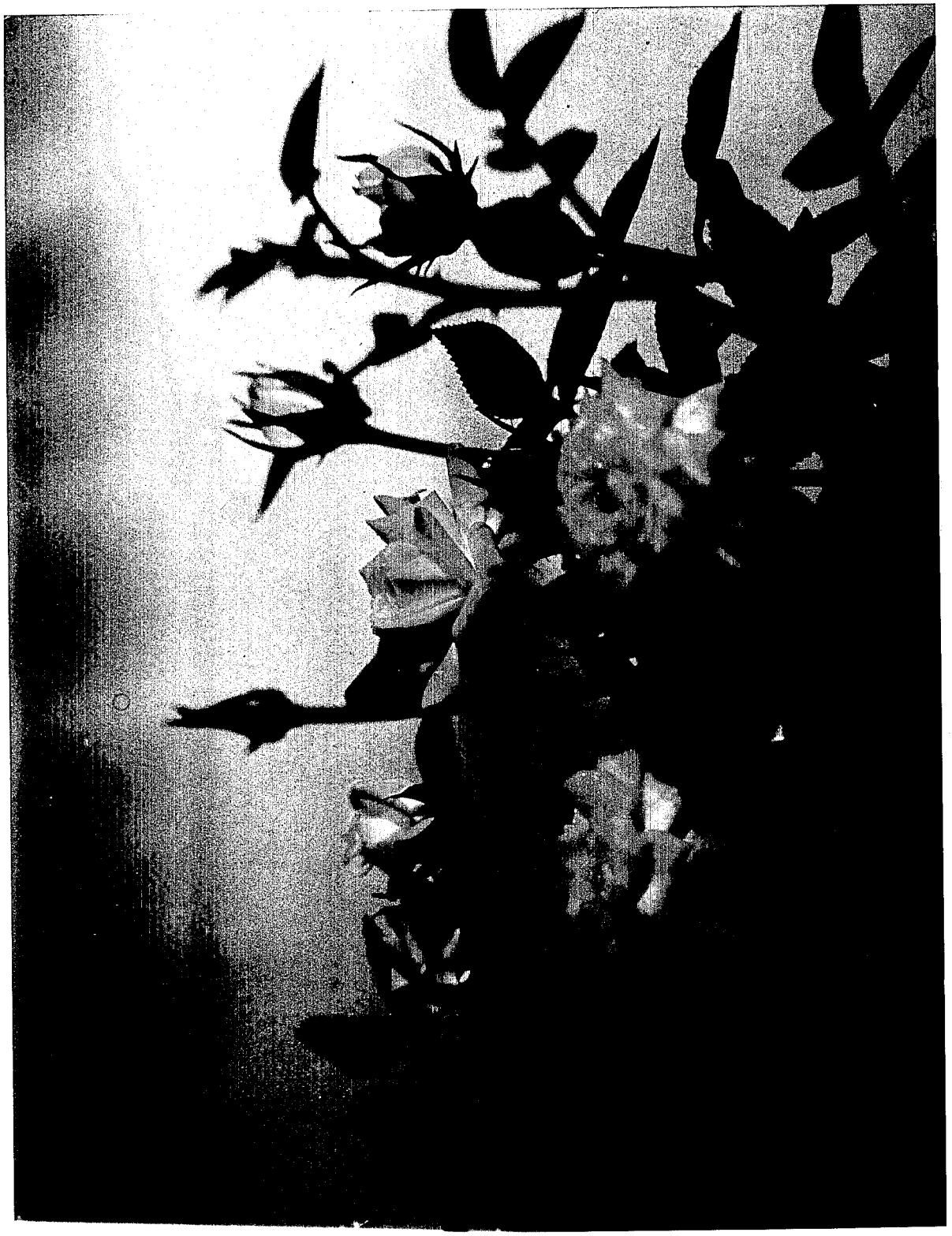

* * * * *